(12) United States Patent
Kamalakaran et al.

(10) Patent No.: US 10,685,740 B2
(45) Date of Patent: Jun. 16, 2020

(54) INFECTION MANAGEMENT AND CONTROL

(71) Applicant: KONINKLIJKE PHILIPS N.V., Eindhoven (NL)

(72) Inventors: Sitharthan Kamalakaran, Pelham, NY (US); Pramod Mayigowda, White Plains, NY (US); Henry Lin, Quincy, MA (US); Sonia Chothani, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 319 days.

(21) Appl. No.: 15/557,269

(22) PCT Filed: Mar. 10, 2016

(86) PCT No.: PCT/EP2016/055195
§ 371 (c)(1),
(2) Date: Sep. 11, 2017

(87) PCT Pub. No.: WO2016/142493
PCT Pub. Date: Sep. 15, 2016

(65) Prior Publication Data
US 2018/0052954 A1 Feb. 22, 2018

Related U.S. Application Data

(60) Provisional application No. 62/132,168, filed on Mar. 12, 2015.

(51) Int. Cl.
*G16B 45/00* (2019.01)
*G16H 10/60* (2018.01)
*G16H 40/63* (2018.01)

(52) U.S. Cl.
CPC .............. *G16B 45/00* (2019.02); *G16H 10/60* (2018.01); *G16H 40/63* (2018.01)

(58) Field of Classification Search
CPC ...................................................... G16H 10/60
See application file for complete search history.

(56) References Cited

U.S. PATENT DOCUMENTS

| 2002/0120408 | A1* | 8/2002 | Kreiswirth | ............. | C12Q 1/689 |
| | | | | | 702/20 |
| 2006/0241978 | A1* | 10/2006 | Yoshii | .................... | G06Q 50/24 |
| | | | | | 705/3 |
| 2007/0225918 | A1 | 9/2007 | Hinrichs et al. | | |
| 2009/0183095 | A1 | 7/2009 | Deitsch et al. | | |
| 2010/0169810 | A1 | 7/2010 | Ruoff et al. | | |
| 2010/0281401 | A1 | 11/2010 | Tebbs et al. | | |
| 2015/0234981 | A1 | 8/2015 | Naidich | | |

FOREIGN PATENT DOCUMENTS

| CA | 2592705 A1 | 12/2008 |
| JP | 2004234459 A | 8/2004 |
| JP | 2014146155 A | 8/2014 |
| JP | 2014209356 A | 11/2014 |

* cited by examiner

*Primary Examiner* — Sheetal R Paulson

(57) ABSTRACT

Methods and systems for monitoring and determining antimicrobial resistance and antimicrobial treatment using genomic subtype information. Various embodiments utilize molecular epidemiology and next-generation sequencing technologies (NGS) to monitor multi-drug resistant pathogens and provide early insight into emergent microbial threats.

18 Claims, 10 Drawing Sheets

INFECTION MANAGEMENT AND CONTROL

CROSS-REFERENCE TO PRIOR APPLICATIONS

This application is the U.S. National Phase application under 35 U.S.C. § 371 of International Application No. PCT/EP2016/055195, filed on Mar. 10, 2016, which claims the benefit of U.S. Provisional Application Ser. No. 62/132,168, filed Mar. 12, 2015. These applications are hereby incorporated by reference herein, for all purposes.

FIELD

Various embodiments described herein generally relate to the management and control of infections, and more specifically to the use of genomic data for infection control and management.

BACKGROUND

Healthcare-associated infections (HAIs) are infections acquired by patients during healthcare treatments for another condition. HAIs in the medical literature are referred to as "nosocomial" infections. HAIs can be deadly, tend to be ubiquitous, and include both bacterial and fungal causes.

Nosocomial infections can cause severe pneumonia and infections of the urinary tract, bloodstream and other parts of the body. Many types are difficult to attack with antibiotics, and their antibiotic resistance is spreading to Gram-negative bacteria that can infect people outside the hospital environment. In the United States, the most frequent type of infection in the hospital context is urinary tract infection (36%), followed by surgical site infection (20%), and then bloodstream infection and pneumonia (both 11%).

Approximately 1 out of every 25 patients hospitalized will contact an HAI. A study conducted in 2011 estimated that there were approximately 722,000 HAIs in U.S. acute care hospitals. About 75,000 hospital patients with HAIs died during their hospitalization and more than half of those patients were treated outside the intensive care unit.

The significant economic consequences of HAIs were published in 1992 based on the Study on the Efficacy of Nosocomial Infection Control (SENIC), a study conducted in the mid-1970s. At the time of publication, the direct cost of HAIs on healthcare was estimated at $6.65 billion (adjusted for inflation). However, recent published evidence puts HAI direct costs today between $28.4 and $33.8 billion dollars. Much of this cost is related to longer patient stays, quarantining parts of the hospital, and discovering and eradicating the source of infection.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

There is a need for methods and systems that allow for the improved management and control of infections, especially in a clinical environment. The rise of affordable genome sequencing technologies provides a growing opportunity to aid medical practitioners in the task of managing and preventing healthcare-associated infections. Various embodiments utilize genomic sequencing data from an infection site to generate actionable information to help an infection control department and other hospital employees manage and contain healthcare-associated infections.

In particular, various embodiments compare the sequence from one isolate with sequences from other samples taken from patients in the hospital, both contemporaneous and historical, to determine the path of infection, e.g., if another patient may have inadvertently transmitted the disease. Various embodiments can also track commonalities between patients using genomic and clinical information to help practitioners determine potential causes of transmission (e.g., shared medical equipment, etc.).

In one aspect, various embodiments relate to a computer-implemented method for generating a hybrid display of genomic and clinical data. The method includes providing a computer processor configured to receive genomic data describing at least one genome isolated from at least one patient; receive electronic patient data; and provide a graphical display of at least a subset of the electronic patient data selected using the genomic data.

In one embodiment the graphical display comprises a user interface element that, when selected, implements an action associated with infection control. In one embodiment the graphical display is a plot of commonalities. The commonalities may be, for example, infection mode commonalities.

In one embodiment the graphical display is a list of patients infected by an organism associated with the genomic data, wherein at least one listed patient shares at least one infection mode commonality with another listed patient and such patients are highlighted in the list of patients. In one embodiment the graphical display is a tree view of patients infected by an organism associated with the genomic data, with each node in the tree representing an infected patient and each link in the tree connecting two nodes whose patients are infected with strains of the organism with similar genomes.

In one embodiment the graphical display is a matrix view where each row is a room from a hospital ward, each column is a bed associated with the room, each patient is displayed in association with at least one bed that they occupied, and each patient display is distinguished according to the genomic data isolated from that patient. In one embodiment the graphical display presents in juxtaposition patients having similar isolated genomic data. In one embodiment the graphical display is an antibiogram for a plurality of target organisms associated with the genomic data and a plurality of antimicrobials. In one embodiment, the graphical display is a timeline display of electronic patient data for patients infected with an organism associated with the genomic data.

In another aspect, various embodiments relate to a computer-readable medium containing computer-executable instructions for performing a method for generating a hybrid display of genomic and clinical data. The medium includes computer-executable instructions for receiving genomic data describing at least one genome isolated from at least one patient; computer-executable instructions for receiving electronic patient data; and computer-executable instructions for providing a graphical display of at least a subset of the electronic patient data selected using the genomic data.

In one embodiment the graphical display comprises a user interface element that, when selected, implements an action associated with infection control. In one embodiment the graphical display is a plot of commonalities. The commonalities may be, for example, infection mode commonalities.

In one embodiment the graphical display is a list of patients infected by an organism associated with the genomic data, wherein at least one listed patient shares at least one infection mode commonality with another listed patient and such patients are highlighted in the list of patients. In one embodiment the graphical display is a tree view of patients infected by an organism associated with the genomic data, with each node in the tree representing an infected patient and each link in the tree connecting two nodes whose patients are infected with strains of the organism with similar genomes.

In one embodiment the graphical display is a matrix view where each row is a room from a hospital ward, each column is a bed associated with the room, each patient is displayed in association with at least one bed that they occupied, and each patient display is distinguished according to the genomic data isolated from that patient. In one embodiment the graphical display presents in juxtaposition patients having similar isolated genomic data. In one embodiment the graphical display is an antibiogram for a plurality of target organisms associated with the genomic data and a plurality of antimicrobials. In one embodiment, the graphical display is a timeline display of electronic patient data for patients infected with an organism associated with the genomic data.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

Non-limiting and non-exhaustive embodiments are described with reference to the following figures in which.

Figure 1:
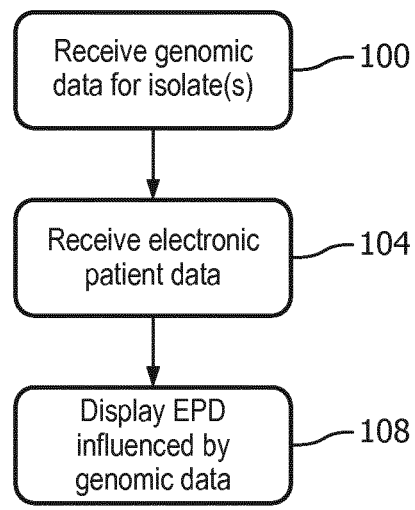
FIG. 1 depicts one embodiment of a method for generating a hybrid display of genomic and clinical data.

Although several of the embodiments depicted in the various figures presented herein focus on particular features, other embodiments include various sets and aspects of these features in combination. Thus, these exemplary figures are non-limiting and specifically are not intended to suggest that such combinations of these features are beyond the scope of the present disclosure.

In the drawings, like reference characters generally refer to corresponding parts throughout the different views. The drawings are not necessarily to scale, emphasis instead being placed on the principles and concepts of operation.

DETAILED DESCRIPTION

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, an entirely software implementation (which will nonetheless be understood to operate on supporting hardware such as a processor) or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one embodiment. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are the means used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic)

quantities within the computer system memories or registers or other such information storage, transmission or display devices.

Certain aspects of the present embodiments described herein include process steps and instructions that could be embodied in software, firmware or hardware, and when embodied in software, could be downloaded to reside on and be operated from different platforms used by a variety of operating systems.

Various embodiments described herein relate to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. As used herein, the term 'processor' will be understood to encompass microprocessors, field-programmable gate arrays (FPGAs), ASICs, and any other similar devices capable or performing the processing functions described herein. Further, as used herein, the term non-transitory machine-readable medium will be understood to encompass both volatile memory devices (e.g., SRAM and DRAM) and non-volatile memory devices (e.g., flash, magnetic, optical memories), but will exclude transitory signals.

The processes and displays presented herein are not inherently related to any particular computer or other apparatus. Various general purpose systems may also be used with programs in accordance with the teachings herein, or it may prove convenient to construct more specialized apparatus to perform the required method steps. The required structure for a variety of these systems will appear from the description below. In addition, various embodiments are not described herein with reference to any particular programming language. It will be appreciated that a variety of programming languages may be used to implement the teachings described herein, and any references below to specific languages are provided for disclosure of enablement and best mode.

In addition, the language used in the specification has been principally selected for readability and instructional purposes, and may not have been selected to delineate or circumscribe the inventive subject matter. Accordingly, the disclosure is intended to be illustrative, but not limiting, of the scope of the invention, which is set forth in the claims.

Various embodiments provide methods and systems for epidemiology and infection management to effectively control transmissions of infectious disease within the clinical environment. Various embodiments identify genomic relationships between isolates of a particular organism and a database of genomic data from past isolates of that organism, as well as automatically collecting and providing easy access to patient and hospital data related to that isolate for the purposes of identifying commonalities and links to help identify the transmission route in the hospital before it becomes an outbreak.

Conventional hospital management dashboards are organized by patient or by the disease they have been admitted for. In contrast, various embodiments organize such data by organism of infection and further allow visualization and analysis of the genomic and clinical information for each type of infection. Consider, for example, two patients infected by the same organism in a clinical environment. A traditional dashboard may list those patients by name, while a dashboard in various embodiments may cluster those patients together, identifying the connection between the two in terms of genomic distance and various other commonalities, such as (but not limited to) devices, procedures, and environmental factors.

These embodiments are useful for individuals involved in infection control and management in a clinical environment, such as hospital administrators, infection prevention specialists, hospital epidemiologists, and infectious disease specialists.

FIG. 1 presents an embodiment of a method for generating a hybrid display of genomic and clinical data. In this embodiment, the process begins with a computing device receiving genomic data describing at least one genome isolated from at least one patient (Step 100). The computing device also receives various electronic patient data (Step 104), such as electronic medical records (EMRs), clinical data (e.g., physician identity), hospital data (locations, procedures, etc.). One of ordinary skill will recognize, of course, that the electronic patient data can be received before, after, or contemporaneously with the receipt of the genomic data (Step 100).

The organism of interest may be isolated by conventional methods such as microbial cultures. The DNA may be extracted from the HAI isolate using, e.g., a Qiagen kit, and sequenced using any of a variety of next-generation sequencing (NGS) technologies (e.g., Illumina Sequencer). The result of the sequencing operation, either full genome sequencing or selective sequencing, is typically, e.g., a Fasta file. The sequencing output is typically aligned against a reference sequence using a publicly-available tool such as BWA or Samtools or, in some embodiments, may be subject to de novo assembly using algorithms such as VELVET to produce longer contiguous sequences. Consensus calls may be determined at each base by using variant caller tools such as varscan.

Once the sequence data has been aligned and/or assembled, the results can be compared against a public or private database of genomic information to identify the particular subtype of the isolate. One such database is the PubMLST dataset, an open-source public database for molecular typing and microbial genome diversity available at http://pubmlst.org/. PubMLST contains a host of bacteria with defined house-keeping genes and their subtypes.

The results of the alignment/assembly step are blasted against a set of house-keeping genes chosen based on the PubMLST criteria for that species. The matching algorithm identifies a matching gene only if it is a 100% match (i.e., in both identity and length), assigns an allele number to that gene, and computes the allele numbers for all of the house-keeping genes of that species. The combination of the allele numbers is used to assign a subtype to the sequenced isolate. The subtype assigned to the isolate, as well as an identification of relevant genes causing drug resistance and virulence, are stored in a genomic data store for later retrieval and display as discussed herein.

Similarities among isolates of the same organism can be identified by comparing the genome of an isolate of interest with the genomes of past isolates of that organism using known methods such as maximum likelihood or nearest neighbor algorithms.

The electronic patient data can be retrieved as needed from a variety of hospital and clinical data sources storing pertinent information such as bed traces, patient information, physician data, location data, etc., using known methods such as HL7 messages using an interoperability or data broker software such as INTELLIBRIDGE ENTERPRISE by KONINKLIJKE PHILIPS N. V. of Eindhoven, Netherlands. In some embodiments, the electronic patient data can be consolidated in a patient data store for later retrieval and display as discussed herein. The consolidation process may be periodic, aperiodic, ongoing, scheduled, etc.

Electronic patient data records may be associated with genomic data for individual isolate samples by, e.g., storing the code for a patient's isolate in that patient's electronic data record. Conversely, an electronic identifier for the patient may be stored in the genomic data store and associated with the records for the isolate.

With these disparate data sets in storage, the computing device proceeds to provide a graphical display of at least a subset of the electronic patient data selected or contextualized using the genomic data (or vice versa; Step 108). For example, if the genomic data relates to a pathogen contained in an isolate, the relevant subset of the electronic patient data may relate to patients carrying the pathogen and the graphical display may utilize that subset, as discussed in greater detail below. In some embodiments, that subset of data may include patients that are presently infected and/or were infected with the pathogen at some point in the past, permitting the comparison of samples in an evolutionary manner to identify the sourcing of transmission, disease spread, HAI, dependencies, commonalities, etc.

Figure 2:
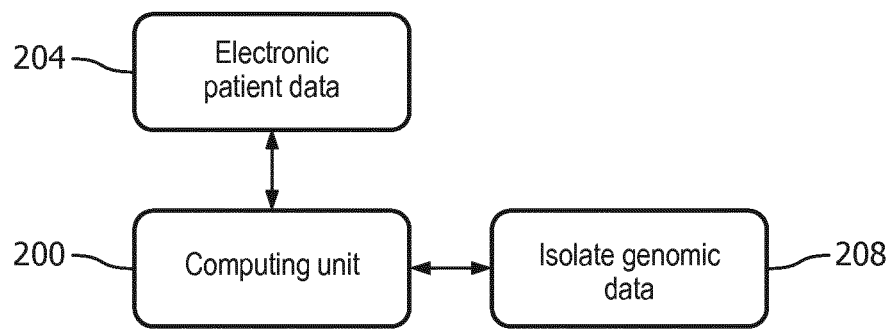
FIG. 2 is a schematic representation of an embodiment of an apparatus for generating a hybrid display of genomic and clinical data.

FIG. 2 is a flowchart of an exemplary system for antibiogram generation. In this embodiment, a computing unit 200 is in communication with a source of electronic patient data 204 and a source of genomic data for at least one isolate 208.

The computing unit 200 may take a variety of forms in various embodiments. Exemplary computing units suitable for use with various embodiments include desktop computers, laptop computers, virtual computers, server computers, smartphones, tablets, phablets, etc. Data sources 204, 208 may also take a variety of forms, including but not limited to structured databases (e.g., SQL databases), unstructured databases (e.g., Hadoop clusters, NoSQL databases), or other data sources running on a variety of computing units (e.g., desktop computers, laptop computers, virtual computers, server computers, smartphones, tablets, phablets, etc.). The computing units may be heterogeneous or homogeneous in various embodiments. In some embodiments, the data source 204 may be an electronic medical records (EMR) system. In some embodiments, the data source 208 may be a piece of testing equipment that determines and stores the genomic data of at least one isolate.

The components of the systems may be interconnected using a variety of network technologies being heterogeneous or homogenous in various embodiments. Suitable network technologies include but are not limited to wired network connections (e.g., Ethernet, gigabit Ethernet, token ring, etc.) and wireless network connections (e.g., Bluetooth, 802.11x, 3G/4G wireless technologies, etc.).

In operation, the computing unit 200 queries the electronic patient data source 204 for information concerning one or more patients that were, e.g., infected with a particular organism in the past or is suspected of presently carrying such an infection. The electronic patient data source 204 may have such information stored locally, or it may contact other computing units or databases to obtain the relevant subtype information as necessary.

In operation, the computing unit 200 queries the genomic data source 208 for information concerning the genome of at least one isolate, often (though not necessarily) an isolate that is also the subject of a query to the electronic patient data source 204. The genomic data source 208 may have such information because it has performed such a test on the isolate, or it may have received such information directly or indirectly (i.e., through data entry or transmission) from a piece of equipment that performed such testing.

Having received the electronic patient data and genomic data for one or more isolates, the computing unit 200 proceeds to generate a graphical presentation of the patient data in combination with the genomic data, as is discussed in greater detail below.

As discussed above, the computing unit 200 may access either data source 204, 208 first or access both data sources contemporaneously. In some embodiments, computing unit 200 is local to an operator, i.e., being located on a local area network accessed by the operator. In other embodiments, computing unit 200 is accessed by an operator over yet another network connection (not shown), such as a wide area network or the Internet, and the graphical presentation is delivered to the operator over such network connection. In these embodiments, the computing unit 200 includes security and web server functionality customary to such remotely-accessed devices.

The hybrid display presented by various embodiments can take a variety of forms, some of which are discussed herein. The hybrid displays in their various forms present a subset of the electronic patient data as selected or influenced by the genomic data.

Timeline View

Figure 3:
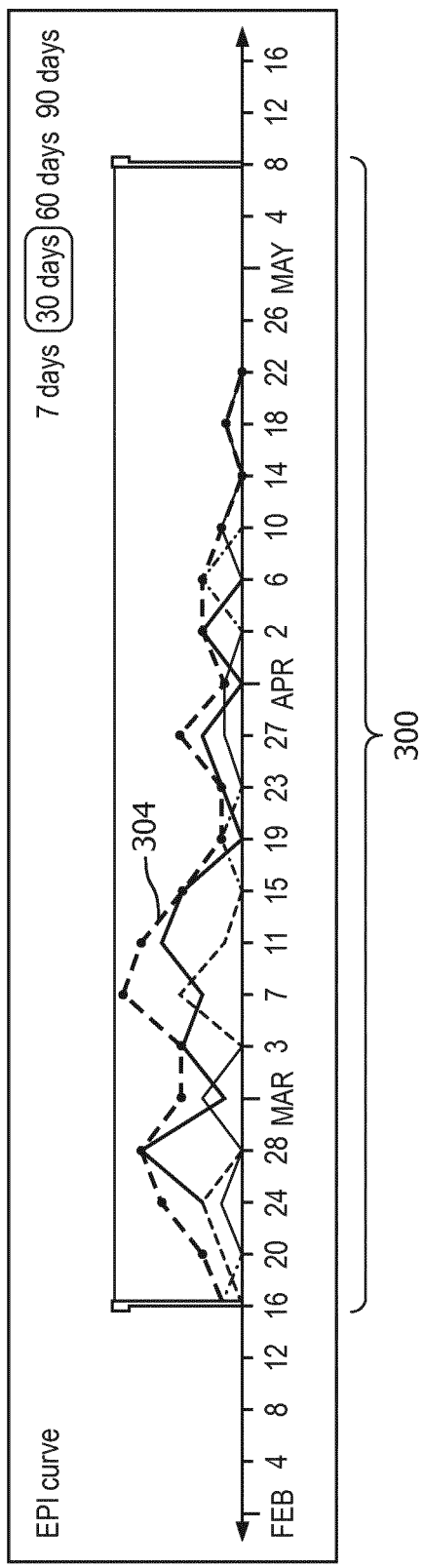
FIG. 3 is an example of a hybrid display of genomic and clinical data as a timeline generated by various embodiments.

Various embodiments permit the summarization of data from isolates for a time period of interest. FIG. 3 presents a timeline view 300 of the sequencing data for the isolate as well as the historical records of other isolates of that organism. The timeline view can appear as a discrete view, as in FIG. 3, or as a component in other composite views, such as the displays presented below in FIGS. 5, 6, and 8-11.

The timeline is interactive, in that a part of the timeline can be selected graphically to select a chronological subset of the displayed isolate records. If the user selects such a subset, then the rest of the display will typically update to present statistics and figures associated with the selected subset of the records.

The timeline view also includes an epidemic curve 304 that presents a graphical display of the numbers of incident cases plotted over time. The form of the distribution of cases can be used to propose hypotheses on the nature of the disease and its mode of transmission.

Overview Page

For each organism under consideration, the user can look at an overview page (not shown) which tells them the overall statistics of the infections observed of the organism. A typical overview page that includes a timeline (as discussed above), a phylogeny tree, an antibiogram, and a commonalities plot.

Figure 4:
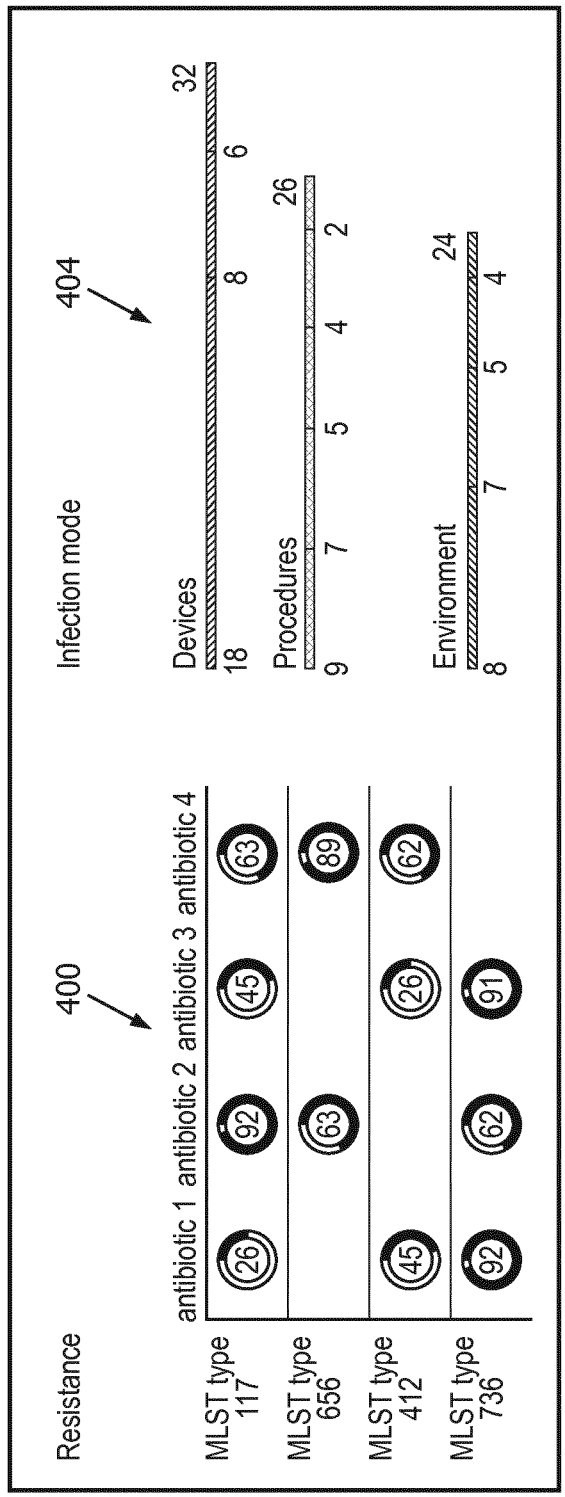
FIG. 4 is an example of a hybrid display of genomic and clinical data as an antibiogram and a plot of infection mode commonalities generated by various embodiments.

FIG. 4 presents an example of an antibiogram 400 and a commonalities plot 404. The antibiogram 400 describes the susceptibility of the various subtypes of the organism to various antimicrobials and helps the healthcare professional determine what antibiotic to use for a patient based on genomic information. The commonalities plot 404 shows the devices, procedures, or other environmental factors that are the most common amongst the patients infected with the organism of interest and helps the healthcare professional recognize and work towards the control and elimination of the vectors for infection.

List View

Figure 5:
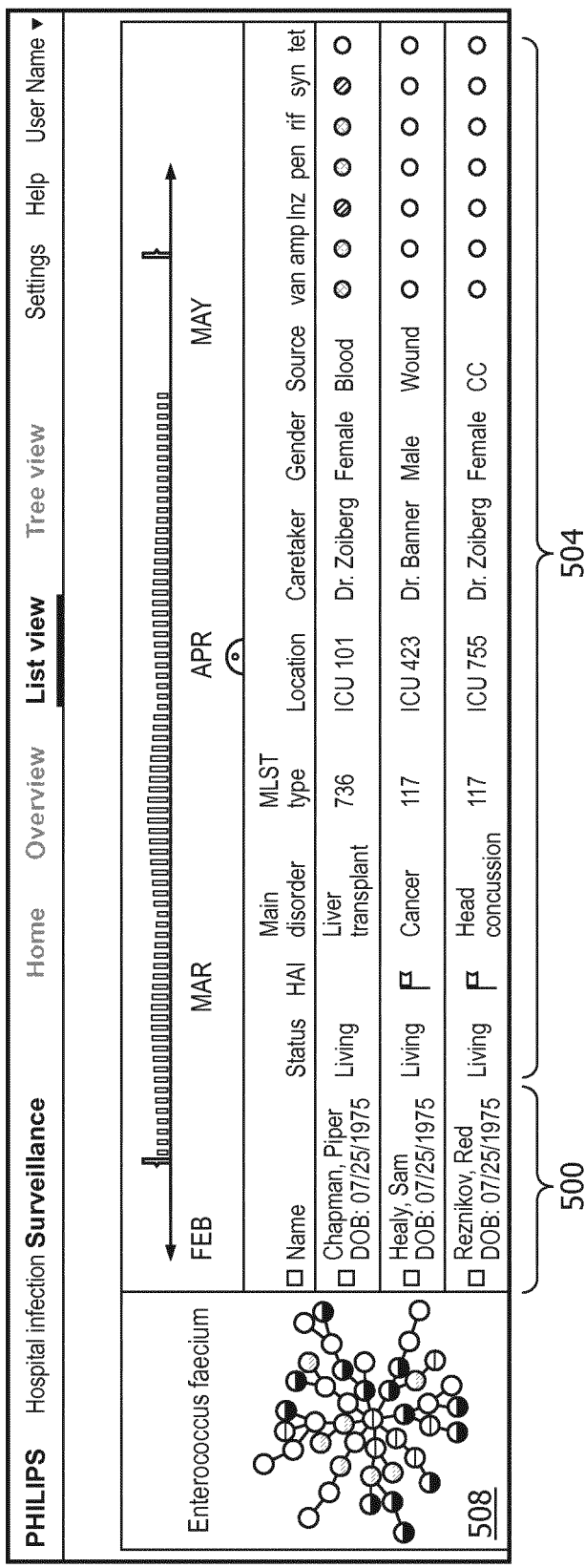
FIG. 5 is an example of a hybrid display of genomic and clinical data as a list view of patients infected by an organism generated by various embodiments.

The user can also review the list view for an organism, an example of which is presented in FIG. 5. The list view presents a list of the patients 500 infected by the isolated organism and the patients' clinical information 504, including but not limited to their healthcare professional, gender, antibiotics, current admission status, etc. This embodiment of the list view also includes an optional timeline component 300, discussed above.

It also shows a thumbnail image of the relationship tree 508 of all these patients based on the genomic analysis of their isolates, discussed in greater detail below. This information is also used to assign HAI flags, which denote that a patient is related to another patient very closely and that there has likely been an infection transmission between these two patients.

In this embodiment, we can select a particular patient and the patient's nearest neighbor in the relationship tree 508 (i.e., their HAI flag partner) and review the clinical information for just the two selected patients. This process can be extended such that the nearest neighbors of those two nearest neighbors are reviewed, and so on.

Tree View

Figure 6:
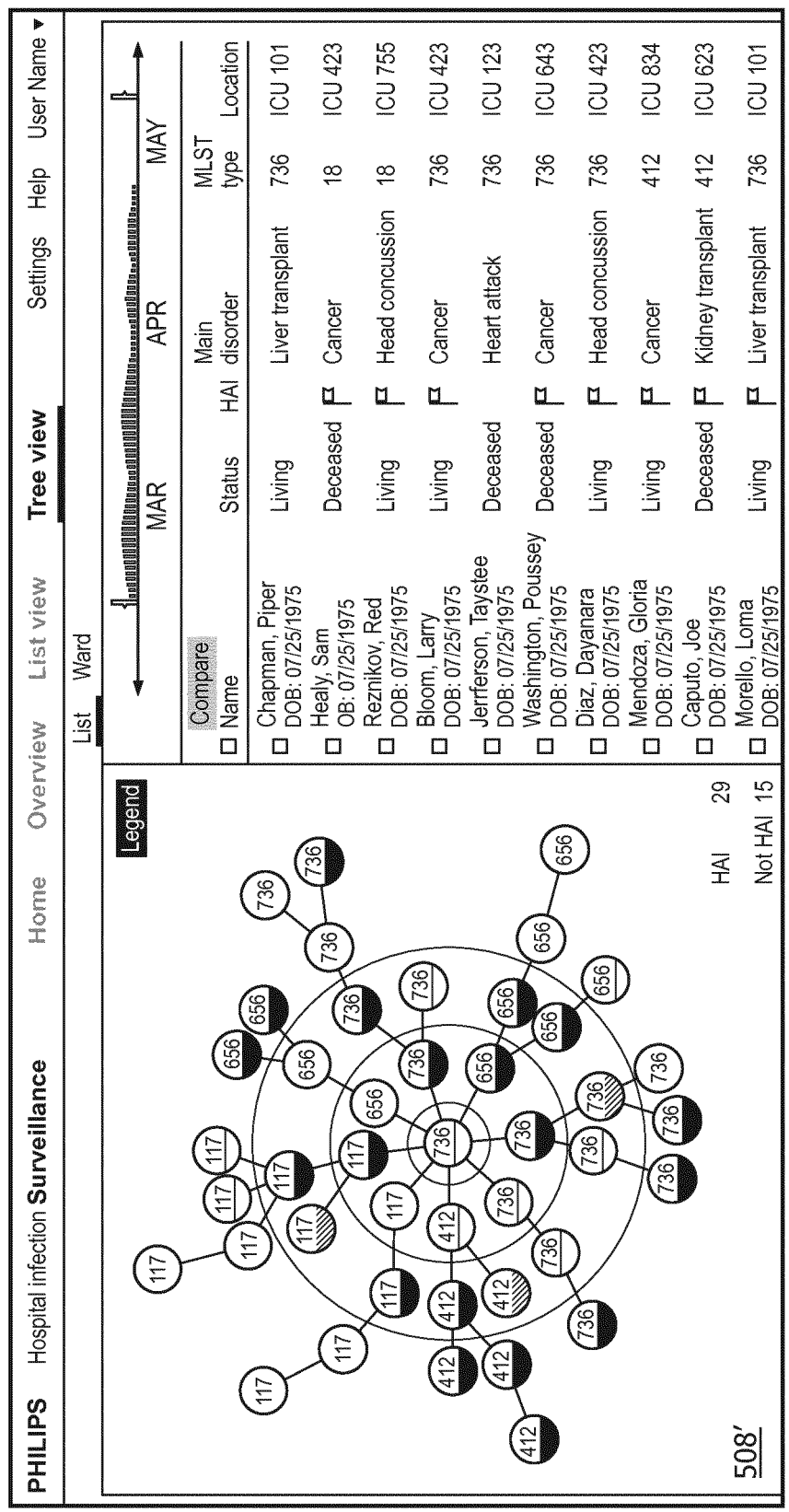
FIG. 6 is an example of a hybrid display of genomic and clinical data as a tree view of patients infected by an organism generated by various embodiments.

Various embodiments also permit the display of a tree view of the patient pool infected with a particular organism, an example of which is presented in FIG. 6. This tree view 508' is built based on the genomic data of the isolates from various patients and overlays clinical information as well. The tree view 508' also allows the user to see the genetic nearest neighbors of each isolate.

Figure 7:
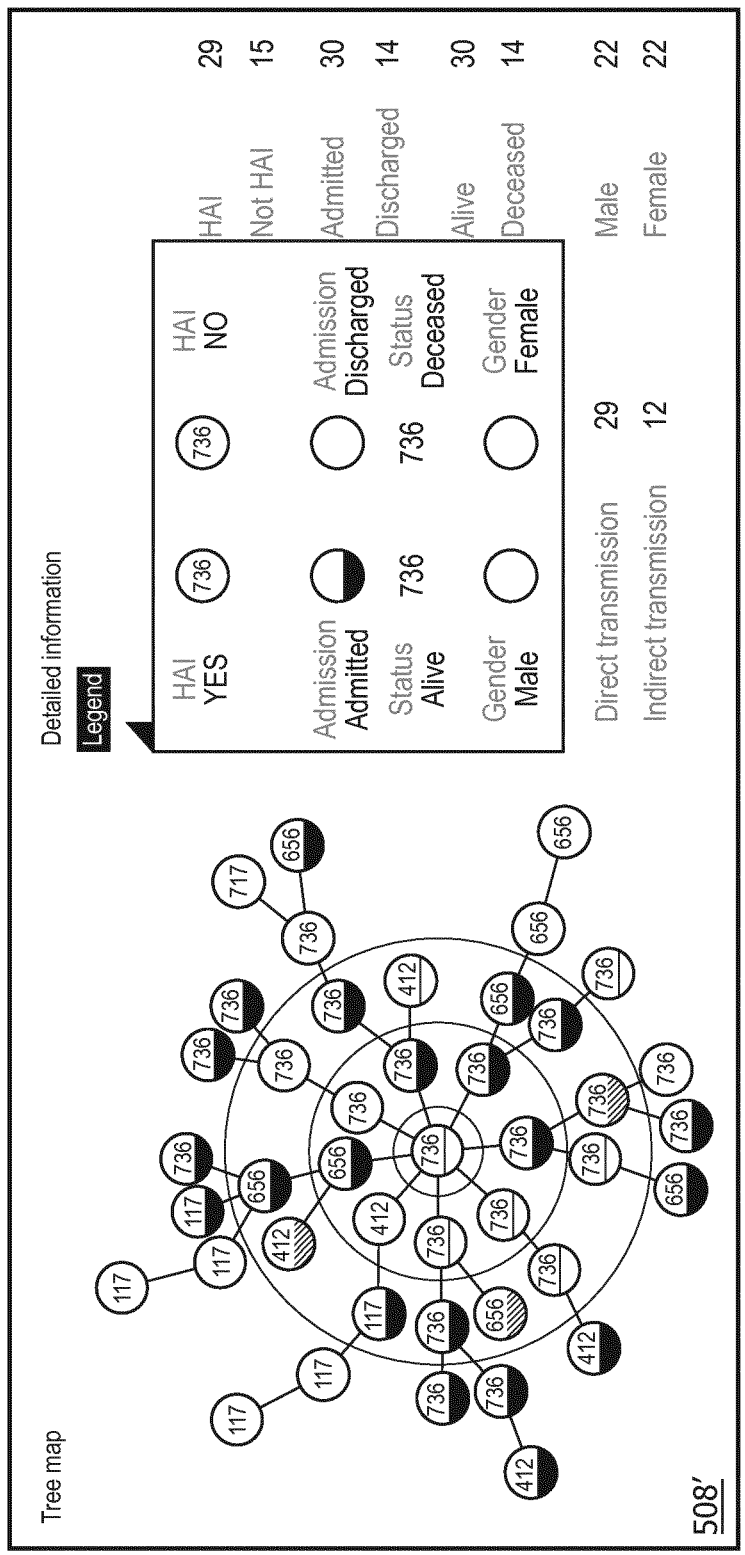
FIG. 7 is the display of FIG. 6 displaying more information concerning one particular subtype of organism.
Figure 8:
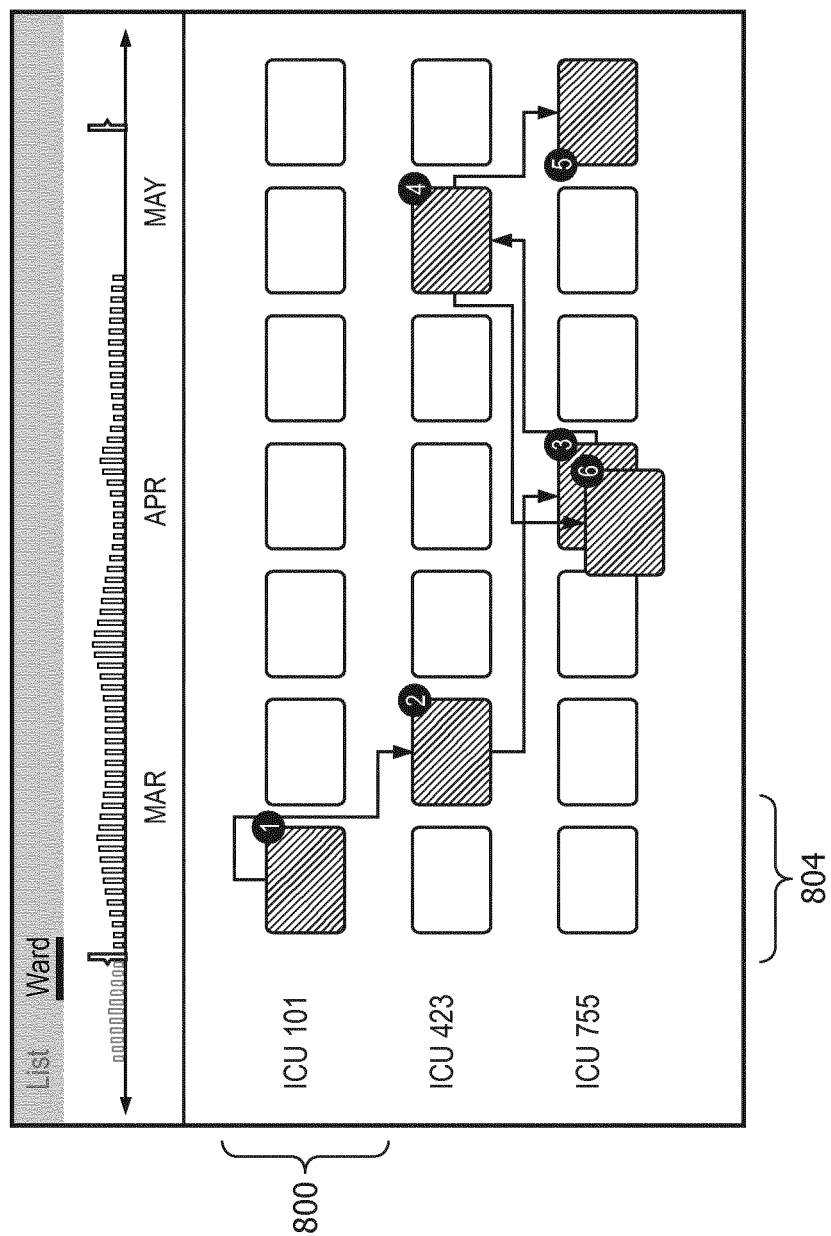
FIG. 8 is an example of a hybrid display of genomic and clinical data as a ward view generated by various embodiments.

As shown in FIG. 7, the tree view 508' represents the relationship amongst all the patients infected by a particular organism. Each node in the tree 508' represents an isolate from a particular patient and an edge is created between two nodes if there is substantial similarity between the genomic sequences associated with the two nodes. Substantial similarity may be determined using genotypic data to create a phylogenetic tree using techniques well-known to one of ordinary skill.

As depicted, clinical information relevant to the patient associated with the isolate associated with the node (like patient health, gender, admission status, etc.) and also genomic information (like organism subtype) associated with the isolate may be displayed in juxtaposition with the tree view 508'.

Ward View

Some various embodiments present a graphical display that allows visualization of the spread of infection in the hospital with respect to each patient's bed. An example of this ward view is presented in FIG. 8, with each row 800 in the view representing a particular room and each column 804 representing a particular bed.

The image shows the sequence of infection among patients on this ward layout and the overlap of Patient 3 and Patient 6 represents that these two patients occupied the same bed.

Exemplary Embodiment

Figure 9:
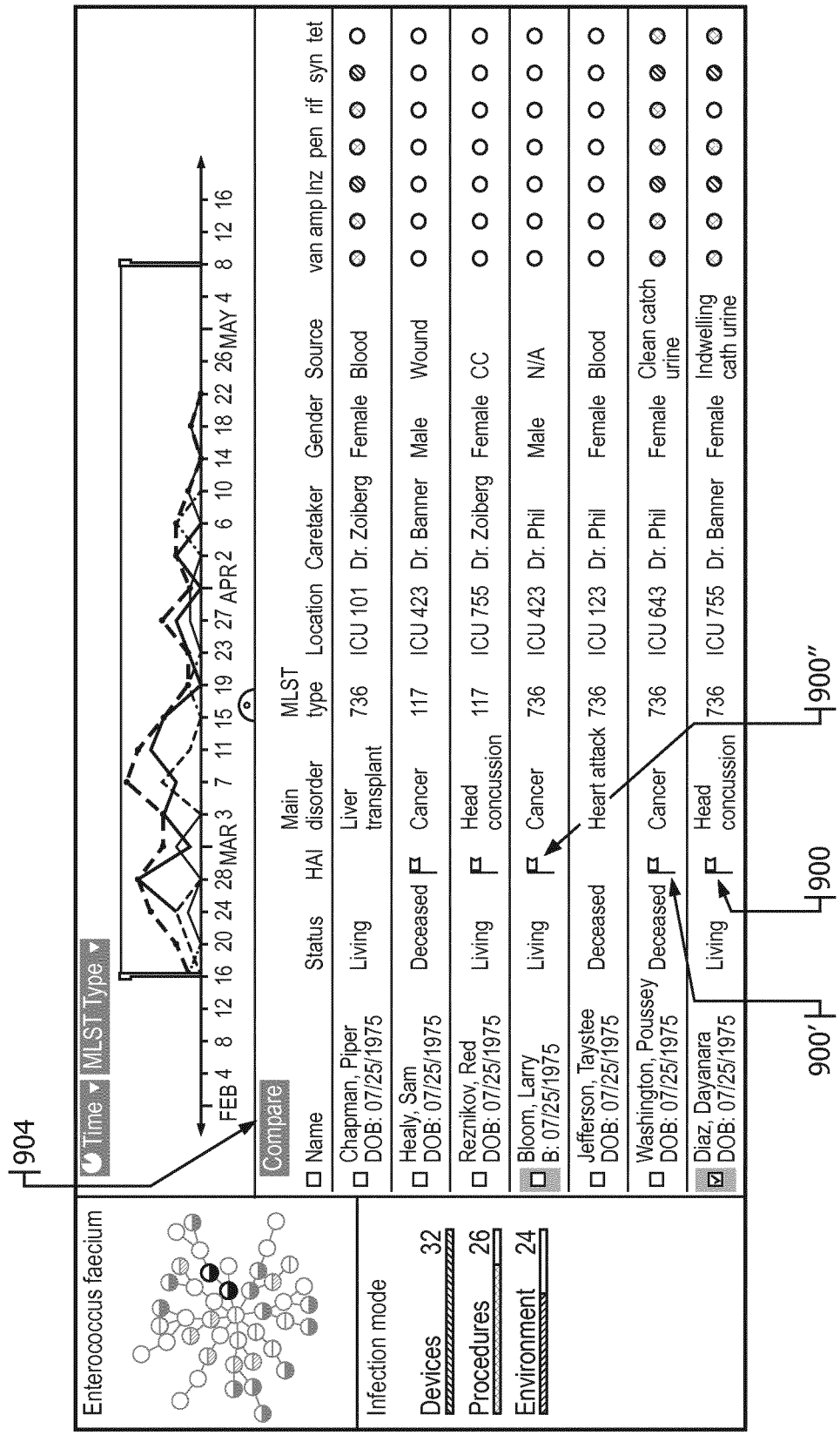
FIG. 9 is an example of a hybrid display of genomic and clinical data as a list view of patients infected by an organism generated by various embodiments.
Figure 10:
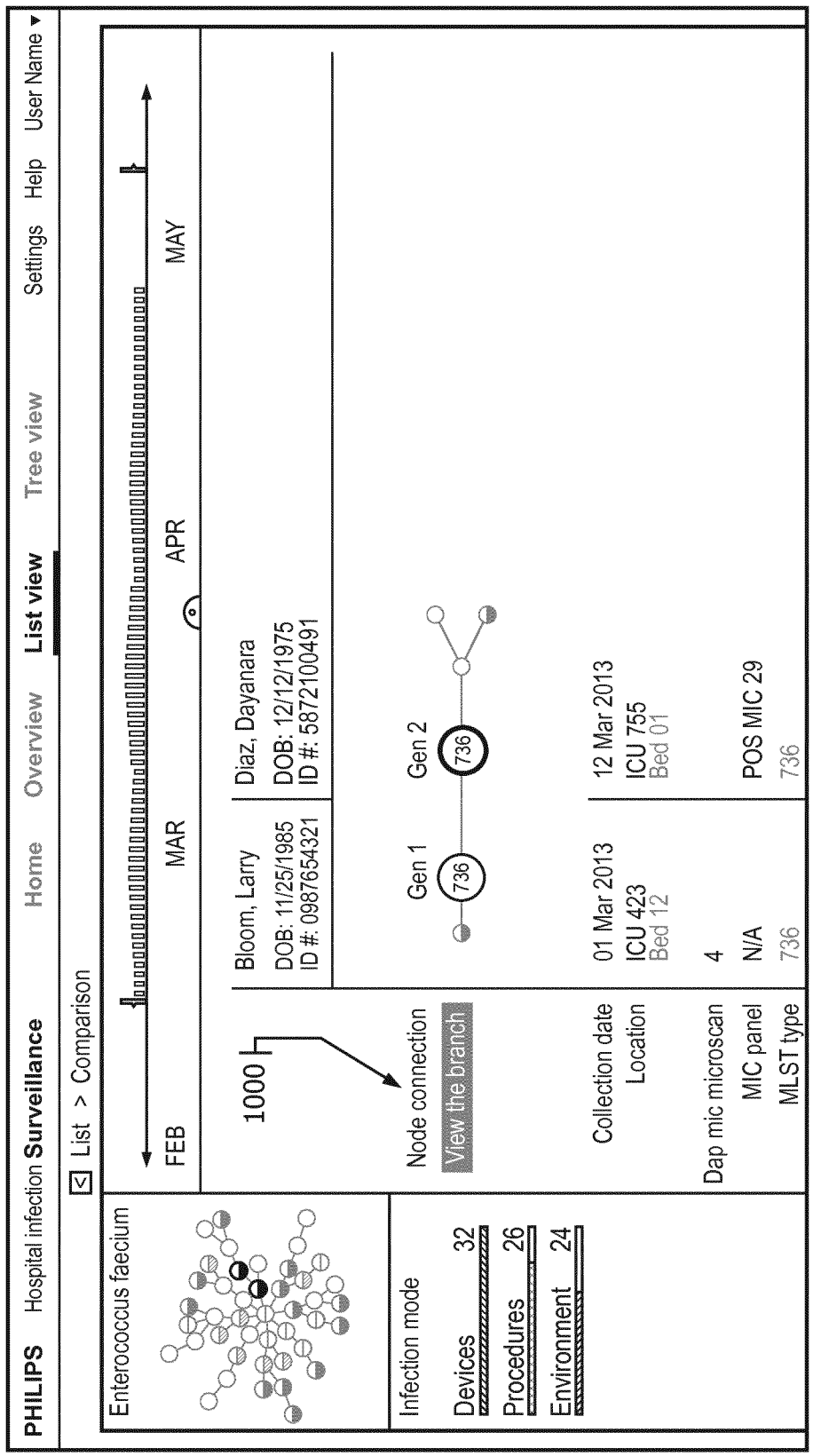
FIG. 10 is an example of a hybrid display of genomic and clinical data as a view of commonalities between patients infected by an organism generated by various embodiments.
Figure 11:
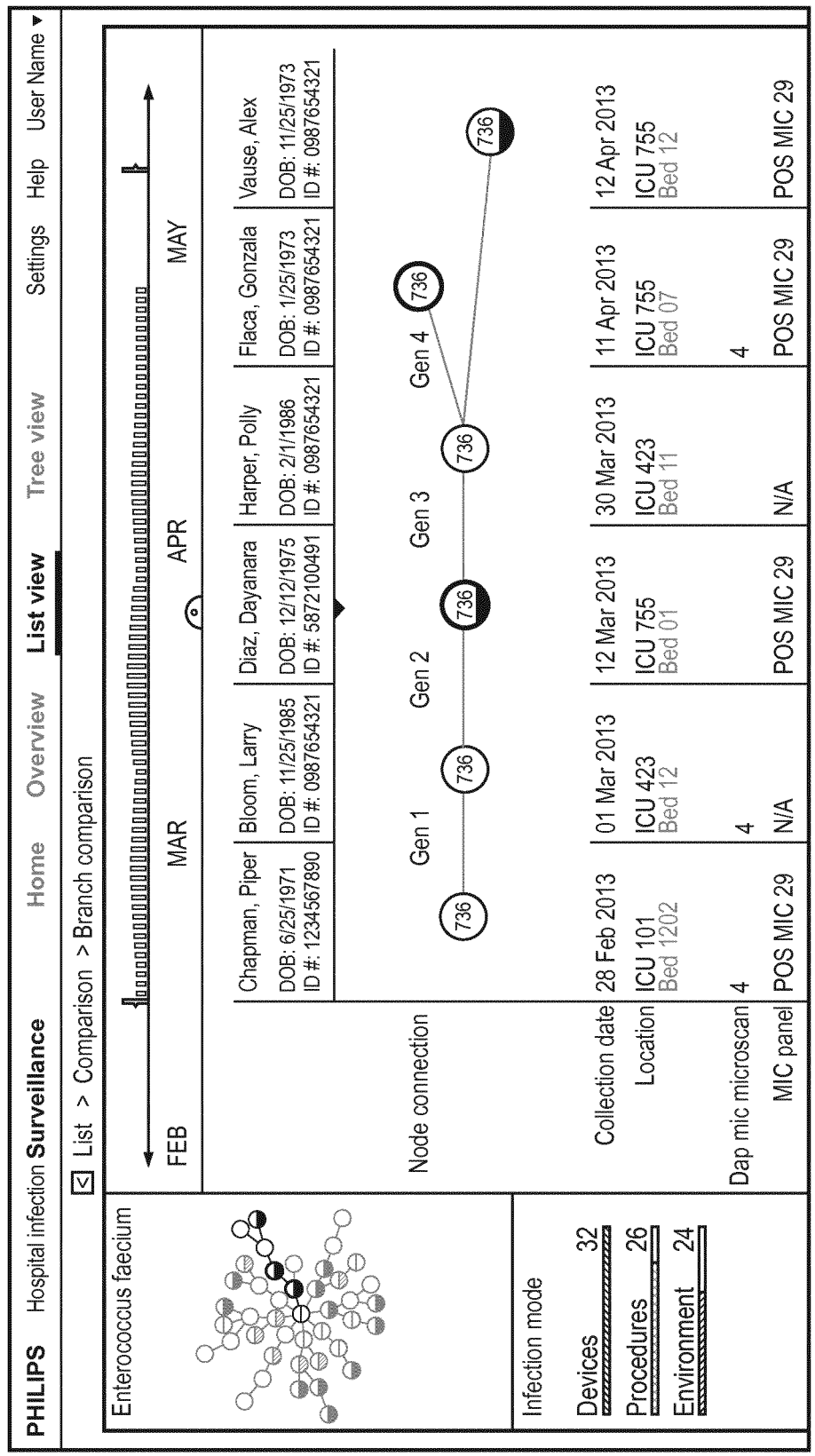
FIG. 11 is an example of a hybrid display of genomic and clinical data as a branch view of patients infected by an organism generated by various embodiments.

FIGS. 9-11 present an exemplary embodiment applied to a study of *E. faecium* in a clinical environment. A plurality of samples are isolated from patients known to be infected with the organism and the samples are sequenced. After sequencing, further processing is carried out for each isolate, including but not limited to MLST finding, SNP differences, tree generation, HAI detection, etc.

FIG. 9 presents a list view of the isolates, as discussed above. Notably, several of the samples are determined to be hospital acquired infections by the analysis and they are indicated as such through the use of flags 900.

Selecting two infected patients by checking the checkboxes next to their names, followed by the selection of the "COMPARE" button 904 launches a new display of the commonalities between the selected patients. The commonalities display is presented in FIG. 10.

Selecting the "VIEW THE BRANCH" button 1000 launches a display of the next nearest neighbors for each of the selected two patients and allows for their comparison in a list view or a branch view. This nearest neighbors view is presented in FIG. 11.

By reviewing these displays, an operator can determine the most virulent source of the organism and contain the source to prevent the further spread of the infection. This information may also help determine appropriate antibiotic treatment for the infected patients.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. A computer-implemented method for controlling a healthcare-associated infection, the method comprising:
   providing a computer processor configured to:
     receive genomic data describing at least one genome isolated from at least two patients;
     receive electronic patient data for the at least two patients who are infected by an organism associated with the genomic data;

determine a genomic distance between the genomic data from the at least two patients;

determine a commonality for the at least two patients within the electronic patient data;

provide a graphical display of at least a subset of the electronic patient data selected using the genomic data, wherein the graphical display includes a list of at least the at least two patients infected by the organism associated with the genomic data, wherein at least one listed patient shares at least one infection mode commonality with another listed patient and such patients are highlighted in the list of patients, wherein the at least one infection mode commonality comprises devices or procedures; and generate actionable information in the graphical display to assist a user in determining an antimicrobial to be administered to at least one of the at least two patients to prevent a healthcare-associated infection from spreading.

2. The computer-implemented method of claim 1, wherein the graphical display comprises a user interface element that, when selected, implements an action associated with infection control.

3. The computer-implemented method of claim 1, wherein the graphical display is a plot of commonalities.

4. The computer-implemented method of claim 3, wherein the commonalities are infection mode commonalities.

5. The computer-implemented method of claim 1, wherein the graphical display is a tree view of patients infected by the organism associated with the genomic data, with each node in the tree representing an infected patient and each link in the tree connecting two nodes whose patients are infected with strains of the organism with similar genomes.

6. The computer-implemented method of claim 1, wherein the graphical display is a matrix view where each row is a room from a hospital ward, each column is a bed associated with the room, each patient is displayed in association with at least one bed that they occupied, and each patient display is distinguished according to the genomic data isolated from that patient.

7. The computer-implemented method of claim 1, wherein the graphical display presents in juxtaposition patients having similar isolated genomic data.

8. The computer-implemented method of claim 1, wherein the graphical display is an antibiogram for a plurality of target organisms associated with the genomic data and a plurality of antimicrobials.

9. The computer-implemented method of claim 1, wherein the graphical display is a timeline display of electronic patient data for patients infected with the organism associated with the genomic data.

10. A non-transitory machine-readable medium containing computer-executable instructions for performing a method for controlling a healthcare-associated infection, the medium comprising:

computer-executable instructions configured to receive genomic data describing at least one genome isolated from at least two patients;

computer-executable instructions configured to receive electronic patient data for the at least two patients who are infected by an organism associated with the genomic data;

computer-executable instructions configured to determine a genomic distance between the genomic data from the at least two patients;

computer-executable instructions configured to determine a commonality for the at least two patients within the electronic patient data; and computer-executable instructions configured to provide a graphical display of at least a subset of the electronic patient data selected using the genomic data, wherein the graphical display includes a list of at least the at least two patients infected by the organism associated with the genomic data, wherein at least one listed patient shares at least one infection mode commonality with another listed patient and such patients are highlighted in the list of patients, wherein the at least one infection mode commonality comprises devices or procedures; and computer-executable instructions configured to generate actionable information in the graphical display to assist a user in determining an antimicrobial to be administered to at least one of the at least two patients to prevent a healthcare-associated infection from spreading.

11. The non-transitory machine-readable medium of claim 10, wherein the graphical display comprises a user interface element that, when selected, implements an action associated with infection control.

12. The non-transitory machine-readable medium of claim 10, wherein the graphical display is a plot of commonalities.

13. The non-transitory machine-readable medium of claim 12, wherein the commonalities are infection mode commonalities.

14. The computer-readable medium of claim 10, wherein the graphical display is a tree view of patients infected by the organism associated with the genomic data, with each node in the tree representing an infected patient and each link in the tree connecting two nodes whose patients are infected with strains of the organism with similar genomes.

15. The computer-readable medium of claim 10, wherein the graphical display is a matrix view where each row is a room from a hospital ward, each column is a bed associated with the room, each patient is displayed in association with at least one bed that they occupied, and each patient display is distinguished according to the genomic data isolated from that patient.

16. The computer-readable medium of claim 10, wherein the graphical display presents in juxtaposition patients having similar isolated genomic data.

17. The computer-readable medium of claim 10, wherein the graphical display is an antibiogram for a plurality of target organisms associated with the genomic data and a plurality of antimicrobials.

18. The computer-readable medium of claim 10, wherein the graphical display is a timeline display of electronic patient data for patients infected with the organism associated with the genomic data.

* * * * *